United States Patent [19]

Brandvold

[11] Patent Number: 5,760,286
[45] Date of Patent: Jun. 2, 1998

[54] PREPARATION OF TERTIARY PHOSPHINE SULFONIC ACIDS

[75] Inventor: Timothy A. Brandvold, Buffalo Grove, Ill.

[73] Assignee: UOP LLC, Des Plaines, Ill.

[21] Appl. No.: 832,594

[22] Filed: Apr. 2, 1997

[51] Int. Cl.$^6$ ............................................. C07F 5/02
[52] U.S. Cl. .................................................. 562/35
[58] Field of Search ...................................... 562/35

[56] References Cited

U.S. PATENT DOCUMENTS 4,716,138  12/1987  Murray ................................. 502/117
4,822,915  4/1989  Murray ................................... 568/13

*Primary Examiner*—Paul J. Killos
*Attorney, Agent, or Firm*—Thomas K. McBride; Eugene I. Snyder

[57] ABSTRACT

Tertiary phosphine sulfonic acids are important ligands for transition metals where the complex is effective in catalyzing the oligomerization of alpha-olefins. An improved method of preparation utilizes inverse addition of lithiated aryl sulfonate salts to dihalophosphines at a rate which maintains a homogeneous reaction mixture, then alkylating the product of this reaction—a monohalo secondary phosphine sulfonate—with an organometallic compound, such as a Grignard reagent or an organolithium species.

8 Claims, No Drawings

PREPARATION OF TERTIARY PHOSPHINE SULFONIC ACIDS

FIELD OF THE INVENTION

This invention relates to the preparation of certain tertiary phosphines. More particularly, the invention is related to the preparation of tertiary phosphine sulfonates which serve as ligands for transition metals, where the resulting complex is an effective catalyst in the oligomerization of alpha-olefins.

BACKGROUND OF THE INVENTION

Linear olefins are one of the most useful classes of hydrocarbons used as raw materials in the petrochemical industry and among these the linear alpha-olefins—unbranched olefins whose double bond is located at a terminus of the chain—form an important subclass. Linear alpha-olefins can be converted to linear primary alcohols by hydroformylation (oxo synthesis); alcohols of carbon number less than eleven are used in the synthesis of plasticizers whereas those of carbon number greater than eleven are used in the synthesis of detergents. Hydroformylation also can be used to prepare aldehydes as the major products which in turn can be oxidized to afford synthetic fatty acids, especially those with an odd carbon number, useful in the production of lubricants. Linear alpha-olefins also are used in the most important class of detergents for domestic use, namely the linear alkylbenzenesulfonates, which are prepared by Friedel-Crafts reaction of benzene with linear olefins followed by sulfonation.

Another important utilization of alpha-olefins is free radical hydrobromination to give primary bromoalkanes which are important intermediates in the production of thiols, amines, amine oxides, and ammonium compounds. Direct sulfonation of the alpha-olefins afford the alpha-olefin sulfonates, a mixture of isomeric alkenesulfonic acids and alkanesulfones, which are effective laundry agents even in hard water and at low concentrations. Linear alpha-olefins, particularly those of eight carbons and under also are used as comonomers in the production of high density polyethylene and linear low density polyethylene.

Although linear olefins are the product of dehydrogenation of linear alkanes, the major portion of such products are the internal olefins. Preparation of alpha-olefins is based largely on oligomerization of ethylene, which has as a corollary that the alpha-olefins produced have an even number of carbon atoms. Oligomerization processes for ethylene are based mainly on organoalumninum compounds or transition metals as catalyst. Using catalytic quantities of, for example, triethylaluminum, the oligomerization of ethylene proceeds at temperatures under 200° C. to afford a mixture of alpha-olefins whose carbon number follows a Poisson or a Schultz-Flory distribution, depending upon the nature of the catalyst, inter alia. In the C6–C10 range there is less than 4% branched alpha-olefins, but the degree of branching increases to about 8% as the chain length is extended to the 18. A modified process, the so-called Ethyl process, affords a high conversion of ethylene to alpha-olefins with a more controlled distribution but product quality suffers dramatically, particularly in the content of branched olefins. Thus, in the C14–C16 range linear alpha-olefins represent only about 76% of the product.

A notable advance in the art accompanied the use of transition metals as catalysts for ethylene oligomerization. The use of, for example, nickel, cobalt, titanium, or zirconium catalysts afforded virtually 100% monoolefins with greater than 97% as alpha-olefins, under 2.5% as branched olefins, and under 2.5% as internal olefins. Since the catalysts are insoluble in hydrocarbons, oligomerization by catalyst systems based on transition metals typically is performed in a polar solvent to solubilize the catalyst. Ethylene and its oligomers have limited solubility in the polar solvents used, consequently the oligomerization process is associated with a 3-phase system; a polar liquid solvent phase containing the catalyst, a second liquid hydrocarbon phase (consisting of the oligomers produced), immiscible with the polar liquid phase, and ethylene in the vapor phase. Such a system permits of a continuous oligomerization process, since ethylene can be introduced into the polar phase and oligomerization products can be withdrawn as the hydrocarbon phase.

One group of effective catalysts utilizes as ligands phosphine sulfonates of the general structure

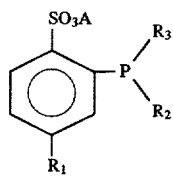

where A = hydrogen, an alkali or alkaline earth metal, a quaternary ammonium or phosphonium group, and the various R groups are hydrogen, alkyl, or aryl groups. The catalyst arising from the foregoing ligands and their utilization in linear alpha olefin oligomerization have been described by Murray in a related series of U.S. patents; see, e.g., U.S. Pat. Nos. 4,716,138 and 4,822,915. Previously the ligands have been prepared by a synthetic route exemplified below for the case where $R_3$=$CH_3$, $R_2$=$C_6H_5$, and $R_3$=n—$C_4H_9$.

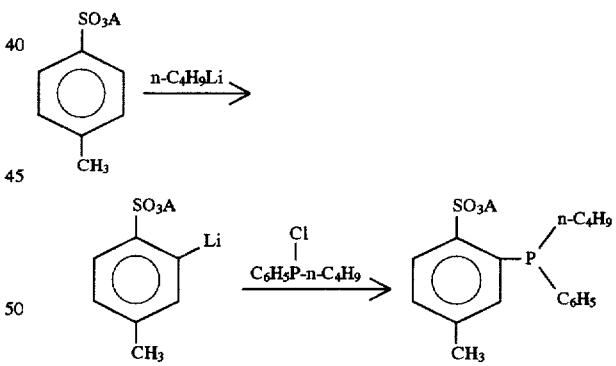

One severe limitation of the synthetic sequence is the general unavailability of monochlorophosphines such as $C_6H_5$(n—$C_4H_9$)PCl and their analogs. Thus, the preparation of such materials itself can be onerous and a serious limitation on the availability of desirable, catalytically effective ligands.

Our need to develop a general method of preparing the foregoing ligands in good yield and in relatively high purity from readily available materials led to a variation in the foregoing preparation which is at once relatively minor in procedure and relatively profound in results. In particular, the synthetic method which is our invention can be exemplified by the following sequence

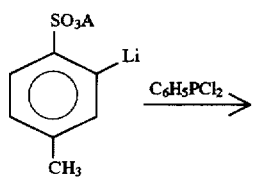

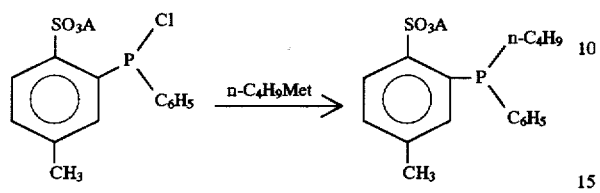

where n—$C_4H_9$Met is an organometallic reagent, such as a Grignard reagent, having the normal butyl group as a reactive anionic component. A key to the foregoing sequence is the inverse addition of sulfonated organolithiums to a dichlorophosphine. This results in the selective formation of the monochlorophosphines whose phosphorus subsequently can be easily alkylated with organometallics to afford ligands of interest in developing suitable catalysts for LAO oligomerization. Since both dichlorophosphines and suitable organometallics are widely available this synthetic route offers versatility and high selectivity, and results in ligand production with high yield. We believe we are the first to recognize that the aforementioned parcel of desirable benefits accrues from the part that inverse addition of sulfonated organolithium to a dichlorophosphine plays in our overall synthetic scheme, and that the benefits of the scheme itself previously were not appreciated.

SUMMARY OF THE INVENTION

The purpose of this invention is to prepare certain tertiary phosphine sulfonates by a more general method which affords a higher product yield with better selectivity. An embodiment comprises the reaction of a sulfonated organolithium with a dihalophosphine via inverse addition of a dispersion of the sulfonated aryl lithium to a solution of the dihalophosphine. In a more specific embodiment the reaction is between equal molar proportions of the sulfonated aryllithium and the dihalophosphine. In a yet more specific embodiment inverse addition is conducted at such a rate that the resulting reaction mixture is at all times homogeneous. Other embodiments will become apparent from the ensuing discussion.

DESCRIPTION OF THE INVENTION

The invention within is the preparation of certain tertiary phosphine sulfonates by the reaction sequence,

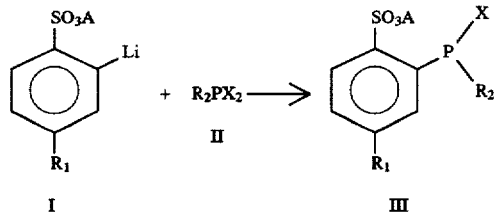

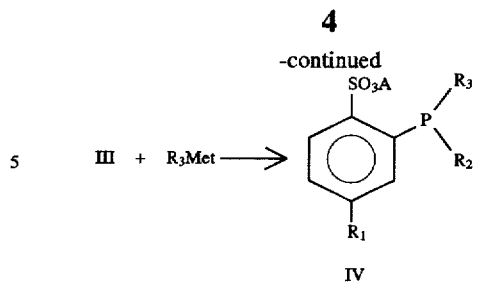

The purpose of the foregoing method is the preparation of IV in high yield and selectivity from materials readily available in commerce. The key to our invention is the inverse addition of I to II. This sequence is termed "inverse" because the common and usual methods of reacting materials analogous to I and II is by addition of II to I. The organolithium (I) is used not as a solution but rather as a dispersion in a suitable organic phase. Hence, a heterogeneous mixture of I is used in the reaction, which is one reason why the usual practice is to add a reagent such as II as a homogeneous phase to a well-stirred heterogeneous dispersion of I. Another feature of our invention is to control the rate of addition of I to II so that the reaction mixture is at all times homogeneous. This always ensures a local excess of II, which in turn is the origin of selectivity.

One of the reactants is metallated aryl sulfonates corresponding to I. Although metals other than lithium may be used, as a practical matter lithiated aryls are the easiest and most convenient of the metallated aryls to prepare and consequently are used almost to the exclusion of other metallated species. The group A in the formula I may be an alkali or alkaline earth metal, or a quaternary ammonium or quaternary phosphonium group. The group $R_1$ may be hydrogen, an alkyl group of 1–20 carbon atoms, or an aryl or aralkyl group. Examples of suitable groups include methyl, ethyl, propyl, butyl, pentyl, hexyl, heptyl octyl, nonyl, decyl, undecyl, and so forth. Exemplary of aryl groups are phenyl, naphthyl, anthryl, biphenyl, and suitable derivatives of these groups. Aralkyl groups are exemplified by benzyl, 1-phenylethyl, 2-phenylethyl, phenylpropyl, and so forth. One important feature is that the lithiated aryl sulfonates are used as a dispersion in an organic phase. The lithiated materials generally are prepared in ether solvents, and tetrahydrofuran is a quite desirable example of such ethers. Materials such as n-butyl lithium (used in the preparation of I) typically are purchased as a solution in hexane, cyclohexane, or pentane. However, the choice of saturated hydrocarbon as the solvent is not particularly critical.

The lithiated aryl sulfonates of formula I are then added as a dispersion in an organic phase to an equal molar proportion of a dihalophosphine, II, as a solution in a suitable organic solvent. The solvents which may be typically used include diethyl ether, dipropyl ether, dibutyl ether, ethyl propyl ether, tetrahydrofuran, tetrahydropyran, dimethyl and diethyl ethers of poly(ethyleneglycol), and so forth. Although chlorine is the halogen most usually utilized in the dihalophosphines, bromine also may suffice even though the use of bromophosphines is relatively infrequent. The group $R_2$ of the dihalophosphine may be an aromatic or fused aromatic group, including biphenyl, an alkyl group containing from 1 up to about 20 carbon atoms, an aralkyl group, and a cycloalkyl group containing between about 5 and 10 ring carbon atoms, as well as substituted analogs thereof. The sole condition which limits the nature of the substituent is that the substituent must be inert to reaction with organometallics. Exemplary of such substituents are alkoxy, aryloxy, fluoro, and fluoroalklyl groups, all of which are virtually universally acceptable. Examples of suitable aryl and alkyl groups have been given previously. Examples of suitable cycloalkyl groups include cyclopentyl, cyclohexyl, cycloheptyl, cyclooctyl, cyclononyl, cyclodecyl, and suitable substituted analogs thereof.

The reaction is conducted between equal molar proportions of I and II, with the dispersion of I added to a solution of II. For greater selectivity it is desired that the local concentration of the lithiated organosulfonate be low relative to the concentration of the dihalophosphine. This condition can be most readily achieved by controlling the rate of addition of I such that the reaction mixture remains homogeneous at all times. By controlling the rate of addition as described above one ensures that one adds the lithiated organosulfonate at a rate no greater than its rate of reaction with the dihalophosphine. This is tantamount to ensuring that the local concentration in the reaction mixture of the lithiated organosulfonate is effectively zero, or close to it.

The reaction product III, which is a monochlorophosphine, is not generally isolated but rather subsequently reacted in situ with an equal molar proportion of a suitable organometallic, $R_3$Met. One class of organometallics often used are Grignard reagents which can be designated as $R_3$MgX, where X is a halogen. Another common organometallic is $R_3$Li, i.e., an organolithium. As to the nature of $R_3$, the only requirement is that it be a group compatible with and unreactive to an organometallic. Thus, suitable groups serving as $R_3$ are hydrogen alkyl groups of 1 to 20 carbon atoms, cycloalkyl groups having 5 to 10 carbon atoms, aryl groups, aralkyl, and substituted analogs thereof. $R_3$ may be an organic group containing nucleophilic heteroatoms, such as primary and secondary amines, their amides, alcohols, and so forth.

The reaction product of III and $R_3$M is a salt of a tertiary phosphine sulfonic acid. Often the salt itself may be used in subsequent complex formation, but where the sulfonic acid is required the sulfonate must be converted to the acid, generally via acidification or ion exchange. The latter processes are so well known that we need not dwell on them beyond their mere mention.

The following example merely illustrates our invention and does not serve to limit it in any way. Many variations will be apparent to the skilled artisan, all of which are intended to be subsumed by our invention.

EXAMPLE

Preparation of 2-Butylphenylphosphinotoluene Sulfonic Acid

Approximately 115 g of lithium tosylate (LiTos) was weighed out and finely ground prior to drying in a nitrogen blanketed, 125° C. oven. After ca. 40 hours of drying, LiTos was removed from the oven and 102 g added to a nitrogen blanketed, 3 liter, 3-necked, round-bottomed flask fitted with overhead stirrer, pressure equalizing addition funnel and thermowell, which was placed into a saltwater ice bath. Next, 750 mL of tetrahydrofuran (THF) was charged to an addition funnel and added to the LiTos. The resulting colorless slurry was stirred until the temperature reached 2.5° C. At this time, 230 mL of n-butyllithium (2.5M solution in hexane) was charged to the addition funnel and added to the LiTos slurry dropwise over the next four hours. Temperature during the addition was maintained <9.0° C. After the butyllithium was added, the dispersion was allowed to mix another twenty minutes, during which the temperature reached 9.0° C.

A 3-necked, 5 liter, round-bottomed flask was set up in an ice bath, again maintained under a nitrogen atmosphere, and equipped with an overhead stirrer, pressure equalizing addition funnel and thermowell. 750 mL of THF was charged to the addition funnel and added to the flask. Next, 78 mL (103 g) of neat dichlorophenylphosphine was added to the THF generating a yellow solution. The solution was allowed to stir for ca. 45 minutes, by which time the temperature had reached 1.0° C. The slurry of ortho-lithiated tosylate, prepared as described above, was transferred under positive nitrogen pressure via a double-tipped needle to the solution of dichlorophenylphosphine at a rate such that the reaction mixture was always homogeneous. The temperature range of the reaction mixture during the transfer was between 1.0° C. and ca. 11° C. The resulting solution was allowed to stir for ca. 30 minutes. 230 mL of n-butyllithium (2.5M solution in hexane) was then charged to the addition funnel and added dropwise to the reaction mixture, maintaining a solution temperature of less than 12° C. After the addition was completed, solution was allowed to stir at ice bath temperature for ca. 1 hour and then overnight at room temperature.

The reaction mixture was poured into a 5 liter, one-necked flask and solvent was removed under reduced pressure, first by rotary evaporation (P~30 mm Hg) then on under high vacuum (P<1 mm Hg) for ca. 1 hour to give a yellow foam.

500 mL of deionized, nitrogen-sparged water was added to the contents of the flask and swirled, resulting in an off-white slurry. Next, nitrogen sparged 2N aqueous hydrochloric acid was added until the solution was acidic to pH paper; approximately 400 mL of acid was ultimately added. The mixture was extracted with three 165 mL portions of dichloromethane. The organic extracts were combined and washed with 500 mL of degassed deionized water. The organic phase was then concentrated to dryness.

Crude material, which weighed 209 g, was dissolved with ca. 150 mL of warm (30°–35° C.) dichloromethane and ca. 100 mL of ether was added to precipitate the product. The flask was chilled in an ice water bath for ca. 6 hours and then placed into a 10° C. refrigerator for 48 hours. The resulting solids were collected by suction filtration and dried under vacuum. Recovered product weighed 155 grams representing 80% yield from lithium tosylate.

What is claimed is:

1. A process for the preparation of compounds leaving the formula,

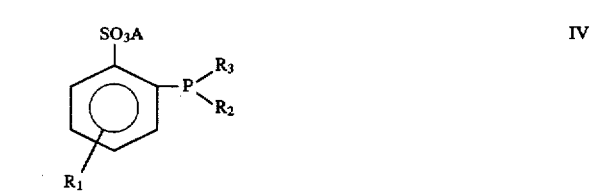

IV where A=H, alkali or alkaline earth metal, quaternary ammonium or phosphonium group, $R_1$ is selected from the group consisting of hydrogen, an alkyl group of from 1 up to about 20 carbon atoms, an aromatic group or an aralkyl group, $R_2$ is selected from the group consisting of an alkyl group of from 1 up to about 20 carbon atoms, an aromatic group or fused aromatic group, an aralkyl group, and a cycloalkyl group having from 5 up to about 10 ring carbon atoms, and $R_3$ is selected from the group consisting of hydrogen, an alkyl group of from 1 up to about 20 carbon atoms, an aromatic group or an aralkyl group, and a cycloalkyl group having from 5 up to about 10 ring carbon atoms, comprising:

a first reaction of compounds of formula II,

   II with compounds of formula I,

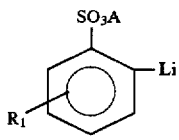   I to afford products of formula III

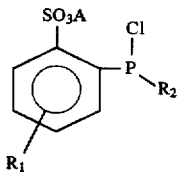   III where said first reaction proceeds by addition of a heterogeneous mixture of one molar proportion of I dispersed in an organic phase to a solution of II in an organic phase to afford a reaction mixture, said addition carried out at a rate such that the reaction mixture is at all times homogeneous, and;

subsequent alkylation of III by an organometallic compound of formula $R_3M$ to afford I, where $R_3M$ is a Grignard reagent or an organolithium.

2. The process of claim 1 where $R_1$ is an alkyl group of 1 up to about 20 carbon atoms.

3. The process of claim 2 where $R_1$ is a methyl group.

4. The process of claim 1 where $R_2$ is an aromatic group.

5. The process of claim 4 where $R_2$ is a phenyl group.

6. The process of claim 1 where $R_3$ is an alkyl group of 1 up to about 20 carbon atoms.

7. The process of claim 6 where $R_3$ is a butyl group.

8. The process of claim 1 where $R_1$ is methyl, $R_2$ is phenyl, and $R_3$ is 2-butyl.

* * * * *

UNITED STATES PATENT AND TRADEMARK OFFICE
CERTIFICATE OF CORRECTION

PATENT NO. : 5,760,286
DATED : June 2, 1998
INVENTOR(S) : Brandvold

It is certified that error appears in the above-indentified patent and that said Letters Patent is hereby corrected as shown below:

Claim 1, line 1, change "leaving" to --having--.

Claim 1, second to the last line, delete "I" and substitute --IV--.

Signed and Sealed this

Eighteenth Day of August, 1998

Attest:

BRUCE LEHMAN

Attesting Officer                Commissioner of Patents and Trademarks